(12) United States Patent
Cai et al.

(10) Patent No.: US 11,365,422 B2
(45) Date of Patent: Jun. 21, 2022

(54) MAPLE-LEAF-TYPE CUCUMBER PLANT

(71) Applicants: Zhuhu Cai, Beijing (CN); Wuzi Cui, Beijing (CN)

(72) Inventors: Zhuhu Cai, Beijing (CN); Wuzi Cui, Beijing (CN)

( * ) Notice: Subject to any disclaimer, the term of this patent is extended or adjusted under 35 U.S.C. 154(b) by 519 days.

(21) Appl. No.: 16/089,326

(22) PCT Filed: Mar. 28, 2016

(86) PCT No.: PCT/CN2016/077535
§ 371 (c)(1),
(2) Date: Sep. 27, 2018

(87) PCT Pub. No.: WO2017/166027
PCT Pub. Date: Oct. 5, 2017

(65) Prior Publication Data
US 2020/0299712 A1    Sep. 24, 2020

(51) Int. Cl.
*C12N 15/82* (2006.01)

(52) U.S. Cl.
CPC .............................. *C12N 15/8262* (2013.01)

(58) Field of Classification Search
None
See application file for complete search history.

(56) References Cited

FOREIGN PATENT DOCUMENTS

| CN | 104450735 A | 3/2015 |
|---|---|---|
| WO | 0216622 A1 | 2/2002 |

OTHER PUBLICATIONS

Reaume (2010 Nature Manitoba Grant, pp. 1-3 (Year: 2010).*
Jiang et al., The source-sink relationship in the process of vegetable production, 1982.
Wang et al., Effect of leaf area index on photosynthesis and yield of winter wheat after anthesis, Plant Nutrition and Fertilizer Science, China Academic Journal Electronic Publishing House, 2012, 18 (1): 27-34.
Wu et al., Cucumber Leaf Area Genetics and QTL Analysis, China Academic Journal Electronic Publishing House, 2009 (24): 43-46.
Zhang et al., The ear-leaf ratio of population is related to yield and water use efficiency in the water-saving cultivation system of winter wheat, ACTA Ecologica Sinica, 2013 vol. 33, No. 12, 3657-3667.
Chen et al. "The Advance of the Study on Genes and their Linkage in Cucumber", Acta Horticulturae Sinica, vol. 27, No. S1; Dec. 30, 2000; ISSN: 0513-353X, pp. 497-498, and figure 1.
Huang et al. "The Genome of the Cucumber, *Cucumis sativus* L." Nature Genetics, vol. 41, No. 12; Dec. 31, 2009; ISSN: 1061-4036, pp. 1275-1281.
Shi et al. "Genetic Mapping of Little Leaf 2(ll2), a Major QTL Controlling Leaf Area in Cucumber", Journal of Agricultural Biotechnology, vol. 22, No. 4; Apr. 25, 2014; ISSN: 1674-7965, abstract and pp. 416-417.

* cited by examiner

*Primary Examiner* — Brent T Page
(74) *Attorney, Agent, or Firm* — Maschoff Brennan (57) ABSTRACT

Provided is a mutant cucumber plant CC81221 having a maple-leaf-type split leaf or a cucumber plant derived therefrom which has a maple-leaf-type leaf single recessive nuclear gene; also provided is a method for breeding, molecular identification, and application of the maple-leaf-type cucumber plant.

3 Claims, 8 Drawing Sheets
Specification includes a Sequence Listing.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: Laboratory synthesis

<400> SEQUENCE: 1
gtccaggttc tcaatcgagc t                                            21

<210> SEQ ID NO 2
<211> LENGTH: 21
<212> TYPE: DNA
<213> ORGANISM: Artificial sequence
<220> FEATURE:
<223> OTHER INFORMATION: Laboratory synthesis

<400> SEQUENCE: 2
gccacgatat tgagaggttc t                                            21
```

MAPLE-LEAF-TYPE CUCUMBER PLANT

TECHNICAL FIELD

The invention relates to the field of plant leaf shape and a breeding method thereof, in particular to a maple-leaf-type cucumber plant, and a breeding method and an identifying method thereof.

BACKGROUND ART

Cucumber (*Cucumis sativus* L.) is a large-leaf sprawling plant, and the photosynthetic area (i.e. the size of the leaf), and the distribution and photosynthetic efficiency of leaves have direct influence on the yield, fruit quality, disease resistance and the like for cucumber cultivation, especially cultivation using off-season facilities in high-latitude area. The leaves are the material basis for plant photosynthesis, and the leaves are also an important platform for the exchange of gas, water and energy in the ecosystem. Leaf area index (LAI), also known as leaf area coefficient, is a dynamic indicator reflecting the size of crop population. Within a certain range, the yield of crop increases with the increase of the leaf area index. When the leaf area index increases to a certain limit, the field is canopied, the light is insufficient, the photosynthetic efficiency is weakened, and the yield is decreased.

In ecology, the leaf area index, as an important structural parameter of the ecosystem, is used to reflect the number of plant leaf surfaces, canopy structure change, plant community vitality and its environmental effect, and it provides structured quantitative information for the description of the material and energy exchange on the surface of the plant canopy, and plays an important role in ecosystem carbon accumulation, vegetation productivity, energy balance of the interaction among soil, plants and atmosphere, and remote sensing of vegetation. Within a certain range, as the leaf area increases, the leaf area index increases, photosynthetic productivity increases, and yield increases. However, if the leaf area is too large, the canopy structure will be unreasonable, light shading will occur among the leaves of the population at the middle and late stage, the photosynthetic productivity will decline, ineffective breathing and water consumption will increase, the source-sink cannot be coordinated, ultimately resulting in a decrease of the yield (Jiang Xianming, 1982; Wang Chengyu et al., 2012; Zhang Yongping et al., 2013). The commercial properties of cucumber fruit such as gloss and color are also greatly affected by light conditions. When the light conditions for the fruit is good, the fruit is bright and has fresh and tender color.

The leaves of wild cucumber (*Cucumis sativus* Var. *hardwickii*) are relatively small, and the leaf area of cultivated cucumber (*Cucumis sativus* Var. *sativus*) subjected to artificial domestication is expanded by 2 to 3 times. Leaf size and shape are important factors for leaf area index, and an appropriate leaf area value is of great significance for determining an ideal plant type of cucumber plants and breeding cucumber varieties with high colony light energy and nutrient utilization.

The leaf area of cucumber is a quantitative character controlled by multiple genes (Wu Peng et al. Chinese Vegetables. 2009. (24): 43-46; Shi Tingting et al. Journal of Agricultural Biotechnology. 2014, 22(4): 415-421). Quantitative characters are susceptible to environmental conditions. It is very difficult to solve the problem of cucumber population structure simply by changing the leaf size by traditional breeding methods, and no significant progress has been made so far.

Common cucumber leaves mainly have six shapes, namely palm-like pentagon, heart-like pentagon, near-circular shape, long pentagon, long triangle, and heart-like triangle (Li Xixiang et al. Crop variety resources. 1999. (3): 27-29).

At present, there are mainly eight genes that have been found to control the shape of cucumber leaves (described according to the List of Cucumber Genes and Characters published in Cucurbit Genetics Cooperative, Gene List 2015 for Cucumber): blunt pointed leaf (bla) (Robinson, 1987a), heart-shaped leaf-1 (cor-1) (Gornitskaya, 1967), heart-shaped leaf-2 (cor-2) (Robinson, 1987c), wrinkled leaf (cr) (Odland and Groff, 1963a), cleft leaf (dvl) (den Nijs and Mackiewicz, 1980), Ginkgo leaf (gi) (John and Wilson, 1952), small leaf (11) (Goode et al., 1980; Wehner et al., 1987), umbrella-shaped leaf (ul) (Den Nijs and de Ponti, 1983).

Among them, the cleft leaf (dvl-1) mutant is obtained from the Polish cucumber variety by mutagenesis induced by ethylenimine, and the true leaves thereof are completely or partially split, so that each leaf becomes 2 to 5 leaflets, with number of the leaflets depending on the growth of the plants. Under optimal growth conditions, several leaves of the mutant will exhibit normal morphology, but most plants can be identified by the first true leaf. Male and female flower corollas have incisions, showing 5 to 7 separate petals. The cleft leaf 2 (dvl-2) mutant is obtained from the cucumber variety Borszczagowski by mutagenesis induced by ethylene imine. After the second true leaf, the leaves are split and the corollas become separate petals.

At present, there is no maple-leaf-type cucumber plant or related report.

SUMMARY OF THE INVENTION

Based on the existing six types of cucumbers with common leaf shapes including palm-like pentagon, heart-like pentagon, near-circular shape, long pentagon, long triangle, and heart-like triangle, the object of the present invention is to provide a maple-leaf-type cucumber plant and its breeding method and molecular identification method.

The inventors used three cucumber inbred lines of TA511 (Tangshan autumn cucumber in China), HA442 (south China-type cucumber with white green color and sparse thorns) and SG321 (smooth and thornless European fresh-eaten cucumber) as the parent materials, and the parent materials were subjected to conventional composite hybridization. In the segregated populations of offspring, recombinant plants with the character of white green and thornless fresh-eaten cucumber occurred, and they were subjected to self-crossing and continuous selection for three generations, and then planted in the experimental greenhouse of Haidian District, Beijing in the spring of 2012. In the plant population of the inbred progeny, the inventors found a naturally-mutated plant with maple-leaf-type leaves, i.e. a cucumber plant with maple-leaf-type leaves. The plant mainly exhibits the following characteristics: beginning to show the characteristic of cleft leaf from the first true leaf stage, and beginning to show an evident characteristic of maple-leaf-type leaf from the second true leaf. The cucumber with maple-leaf-type cleft leaves have palm-like pentagonal cleft leaves, the young leaves just emerging in the early stage have a shape similar to that of pentagonal maple leaves, and the mature leaves each have a central segment that is of long triangular ovate shape and longer than side segments. The inventor named the cucumber inbred line as: CC81221.

After genetic analysis, the character of maple-leaf-type cleft leaves of the cucumber conformed to the genetic law of single recessive nuclear gene. That is, the cleft leaf character of the maple-leaf-type leaf of the present invention is controlled by a single recessive nuclear gene. The inventors named the cleft leaf gene controlling the maple-leaf-type leaves as dvl-3.

Different from dvl and dvl-2, the cucumber plant having the maple-leaf-type cleft leaf gene dvl-3 is the same as common plants in petal, plant height, vein and vegetative growth and reproductive growth and the like, except for the leaf shape.

The present invention provides a maple-leaf-type cucumber plant, which is:

1) a cucumber mutant plant having a single recessive nuclear gene for maple-leaf-type leaf, which is a *Cucumis* plant CC81221 with the accession number CGMCC No. 11285, or 2) a cucumber plant derived from CC81221 and having a single recessive nuclear gene for maple-leaf-type leaf;

wherein, the single recessive nuclear gene for maple-leaf-type leaf is a gene located at the base position of 16383700 to 16385719 on the second chromosome of the cucumber genome, and the base A at position 859 is mutated to T compared with the gene of cucumbers with a common leaf shape.

Figure 1:
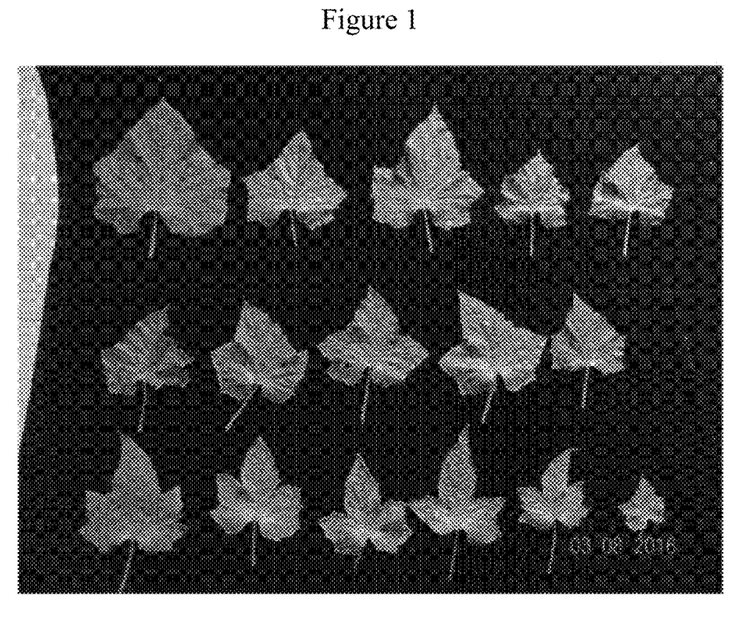
FIG. 1 shows photographs of maple-leaf-type leaves of the present invention, wherein the upper left one is a common leaf, and the rest are maple-leaf-type leaves having different genetic backgrounds.

The maple-leaf-type refers to that the leaves are palm-like pentagonal cleft leaves, wherein the central segment has a long triangular ovate shape and is evidently longer than side segments; the side segments each have a triangular ovate shape, and they are relatively short and shallowly split; and the leaf base is heart-shaped or nearly heart-shaped. When the genetic background is different, the leaf splitting may vary in different degree, that is, the leaves may split shallowly or deeply, and the modification or quantitative variation occurred on the basis of the basic characteristics of maple-leaf-type leaves, such as the central segment being significantly longer, or variation in the width of the segment, or appearance of small protrusions at the leaf base, or the leaf margins being Zigzag or wavy, all fall within the scope of the invention. For details, please refer to FIG. 1, wherein the upper left leaf is a common leaf, and the other leaves are maple-leaf-type leaves with different genetic backgrounds.

Wherein, the derived cucumber plant refers to a new maple-leaf-type cucumber plant obtained by conventional breeding, biotechnological breeding, vegetative propagation or a combination thereof.

Wherein, the conventional breeding includes common breeding methods such as inbreeding, hybridization, and backcrossing, and combinations thereof.

Wherein, the biotechnological breeding includes known biotechnological breeding methods such as transgenic breeding, haplo-diploid breeding and molecular marker breeding, and combinations thereof.

The invention also provides the use of the maple-leaf-type cucumber plant in gardening for sightseeing.

The invention also provides the use of a maple-leaf-type in the variety identification of a maple-leaf-type cucumber plant.

The invention also provides a part of the maple-leaf-type cucumber plant. The part includes, but is not limited to, plant cells, seeds, anthers, pollen, ovules, leaves, germs, roots, root tips, flowers, fruits, stems, shoots, scions, protoplasts or calluses.

The present invention also provides a single recessive nuclear gene for maple-leaf-type leaf, which is a gene located at the base position of 16383700 to 16385719 on the second chromosome of the cucumber genome, and the base A at position 859 is mutated to T compared with the gene of cucumbers with a common leaf shape. This gene is named as dvl-3.

The present invention also provides a vector comprising the single recessive nuclear gene for maple-leaf-type leaf and a host of the vector.

The invention also provides a method for breeding a maple-leaf-type cucumber plant variety, wherein the cucumber variety with maple-leaf-type leaves is bred using CC81221 or a cucumber plant derived from CC81221 and having a single recessive nuclear gene for maple-leaf-type leaf as a genetic source of maple-leaf type.

The breeding is carried out by techniques well known to a person skilled in the art, such as inbreeding and segregation, hybridization, backcrossing, recurrent selection, haploid, tissue culture, mutagenesis or molecular marker-assisted selection, or a combination thereof.

When the breeding method adopts hybridization technology to breed inbred lines, the specific steps are as follows: the maple-leaf-type cucumber plant is hybridized with the cucumber variety A; the plants having the maple-leaf-type gene of the offspring are successively selected and inbred and pedigree breeding is carried out until other agronomic characters are homozygous and no longer segregated; and the plants with maple-leaf-type leaves are selected as inbred lines of the maple-leaf-type cucumber plants. The other agronomic characters are agronomic characters other than cleft leaves, such as plant height, leaf color and other conventional agronomic characters.

When the breeding method adopts backcrossing technology to breed inbred lines, the specific steps are as follows: the maple-leaf-type cucumber plant is hybridized with the cucumber variety B, and the cucumber variety B is used as a recurrent parent to continuously backcrossed with the plants having maple-leaf-type gene; when the characters other than the leaf shape are no longer segregated, inbreeding is carried out for one generation, and plants having other agronomic characters similar to the cucumber variety B and leaves of maple-leaf type are selected as inbred lines of the maple-leaf-type cucumber plants. The plants having the maple-leaf-type gene is selected by the following method:

I. selecting a plant with a single recessive nuclear gene for maple-leaf-type leaf by means of molecular marker, and/or II. selecting the plants having the segregated maple-leaf-type phenotype from the inbred offspring.

The method for breeding inbred lines of maple-leaf-type cucumber plants can also be carried out by breeding via inbreeding and segregating using maple-leaf-type varieties, haplo-diploid breeding, tissue culture, mutation breeding, and the like.

The method for preparing a hybrid variety of maple-leaf-type cucumber plant is as follows: two inbred lines of the maple-leaf-type cucumber plants are selected and hybridized to obtain a hybrid variety of maple-leaf-type cucumber plants.

The invention also provides a molecular identification method for a cucumber plant having a single recessive nuclear gene for maple-leaf-type leaf or a part thereof, and the specific steps are as follows: performing PCR amplification on the plant to be identified with a specific primer pair and sequencing, and determining a cucumber plant having a TT homozygous peak or a cucumber plant having a single recessive nuclear gene for maple-leaf-type leaf with AT heterozygous peak in the sequencing result; the sequences of the specific primer pair are as follows:

upstream primer: GTCCAGGTTCTCAATCGAGCT, as shown in SEQ ID No. 1; and downstream primer: GCCACGATATTGAGAGGTTCT, as shown in SEQ ID No. 2.

The reaction system for PCR amplification is given as follows:

| | |
|---|---|
| 10 μM upstream primer | 1 μl |
| 10 μM downstream primer | 1 μl |
| DNA | 2 μl |
| Premixture (Beijing Liuhetong Trading Co., Ltd., trade name: Premix Taq, product RR901A) | 12.5 μl |
| Sterilized water | the remainder |

The total reaction system is 25 μl.

The reaction conditions for the PCR amplification are given as follows:

Pre-denaturation at 94° C. for 2 min; 30 cycles of denaturation at 94° C. for 30 sec, annealing at 56° C. for 45 sec, and extension at 72° C. for 2.0 min; extension at 72° C. for 15 min, ending at 4° C.

The present invention also provides a primer pair for identifying a cucumber plant having a single recessive nuclear gene for maple-leaf-type leaf or a part of the cucumber plant, the primer pair is given as follows:

upstream primer: GTCCAGGTTCTCAATCGAGCT, as shown in SEQ ID No. 1; and downstream primer: GCCACGATATTGAGAGGTTCT, as shown in SEQ ID No. 2.

The invention has the following advantages:

(1) The cucumber plant having maple-leaf-type leaves provided by the invention enriches the cucumber variety resource and provides a good genetic resource for the cucumber ecological breeding.

(2) The maple-leaf-type leaves of the present invention exhibit high canopy porosity, and less shading to the lower leaves, and correspondingly, the planting density, leaf area index and photosynthetic efficiency are all greatly improved, and the contradictions between planting density and photosynthetic efficiency of population, between vegetative growth and reproductive growth, and the like, which are prevalent but difficult to compromise in cucumber production, are solved.

(3) The plants having maple-leaf-type leaves of the present invention have strong ventilating and light transmitting effect, reduce the occurrence of diseases, correspondingly reduce the use of pesticides, is beneficial to people's health and environmental protection, and reduces production costs.

(4) The maple-leaf-type leave of the present invention, as a discrete character controlled by a single recessive nuclear gene, provides a fast and effective marker for the purity identification and variety identification of cucumber seeds.

(5) The cucumber plant having maple-leaf-type leaves of the present invention is novel and unique, and provides a valuable product for sightseeing agriculture.

(6) The present invention provides a good material basis for cloning the gene and further performing plant breeding on related melons.

BRIEF DESCRIPTION OF THE DRAWINGS (Refer to the Attachments)

SPECIFIC MODES FOR CARRYING OUT THE EMBODIMENTS

The following examples are intended to illustrate the invention but not intended to limit the scope of the invention.

Example 1: Genetic Analysis Experiment of a Maple-Leaf-Type Cucumber Mutant Plant CC81221

(I) Test Materials

Figure 2:
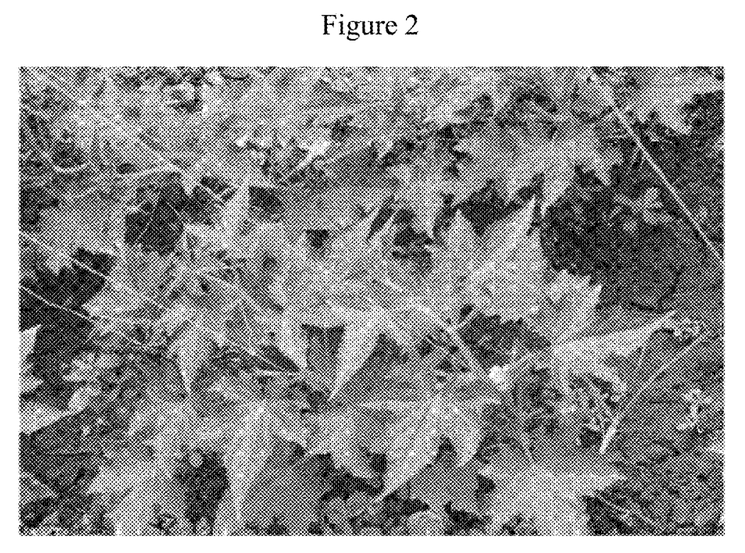
FIG. 2 shows a photograph of the CC81221 maple-leaf-type cucumber plants according to Example 1 in the field.
Figure 3:
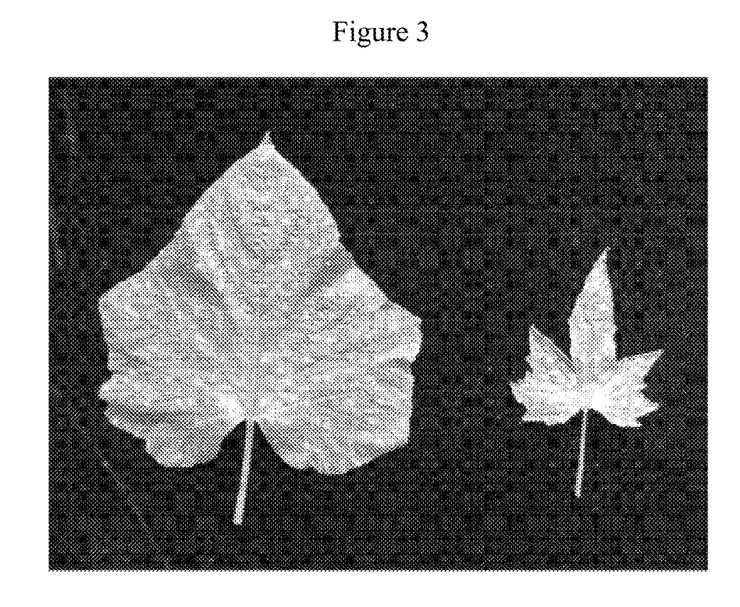
FIG. 3 shows the comparative photograph between the leaf of the CC81221 maple-leaf-type cucumber plant according to Example 1 and a common cucumber leaf, wherein the left one is the common cucumber leaf, and the right one is the leaf of the CC81221 maple-leaf-type cucumber plant.

In the spring of 2012, the inventors planted offspring inbred line materials obtained by multiple composite crosses of the farm variety of Tangshan autumn cucumber, Baiyesan cucumber and European fresh cucumber variety, in the Shangzhuang experimental greenhouse in Haidian District, Beijing, found a maple-leaf-type mutant, and named it as CC81221. The photographs of the mutant are shown in FIG. 2 and FIG. 3.

The *Cucumis sativus* L. CC81221 was deposited in China General Microbiological Culture Collection Center (deposit institution address: Institute of Microbiology, Chinese Academy of Sciences, 3th, No. 1 Courtyard, Beichen West Road, Chaoyang District, Beijing, China) with the accession number of CGMCC No. 11285 on Oct. 16, 2015.

The following cucumbers with a common leaf shape provided by Beijing Beinong Sanyi Cucumber Ecological Breeding Science and Technology Center were used as control varieties:

(1) North China type (dense thorn, palm-like pentagonal leaves): M111

(2) Two inbred lines of the South China type (sparse thorn, palm-like pentagonal leaves), which are:
 (a) Short and thick inbred line TA511 of Tangshan autumn cucumber
 (b) Medium and short inbred line HA411 of dry land cucumber (3) Two inbred lines of European fresh-eaten cucumber (thornless type, heart-like pentagonal leaves), which are:
 (a) inbred line SL311 of green cucumber
 (b) inbred line SL322 of white cucumber (II) Experimental Design Seedlings were transplanted from 50-well plates, wherein 50 seeds were sowed for each of the $F_1$ generation and $BC_1$ generation, and 100 seeds were sowed for the $F_2$ generation.

The combination types were as follows:
(1) Maple-leaf-type: inbreeding
(2) Maple-leaf-type×Common leaf-type→$F_1$→$F_2$
$F_1$×maple-leaf-type
(3) Common leaf-type×maple-leaf-type☐→$F_1$→$F_2$
$F_1$×maple-leaf-type (III) Test Methods (1) In May 2012, in the Shangzhuang Experimental Greenhouse in Haidian District, Beijing, a maple-leaf-type leaf material with the number CC81221 was used as one of the parents, and different types of cucumber inbred lines with common leaves were used as the other parent to obtain direct-cross hybrids and reciprocal-cross hybrids (hybridization of the maple-leaf-type plant as a female parent with the common leaf-type inbred line was defined as direct-cross, and hybridization of the maple-leaf-type plant as a male parent with the common leaf-type inbred line was defined as reciprocal-cross), and harvesting was carried out respectively to give $F_1$ generation.

(2) The $F_1$ generations from various cross combinations were planted, and the leaf shape of the $F_1$ generation plants was observed; one half of the $F_1$ generation plants were selected for inbreeding, and harvesting was carried out respectively to give $F_2$ generation; and the other half of the $F_1$ generation plants were subjected to test cross with CC81221, and $BC_1$ generation seeds were harvested.

(3) The $F_2$ generation and $BC_1$ generation were planted separately, and leaf shape segregation data were observed at the seedling stage and statistics were made.

The results (see Table 1 and Table 2) show that the leaf shapes of the $F_1$ generation plants obtained by hybridization of the maple-leaf-type plant with the common leaf type plant are all common leaf shapes; the segregation ratios (see Table 1) of common leaves to maple-leaf-type leaves in the $F_2$ generation are all 3:1 (common leaves: maple-leaf-type leaves). The ratio of common leaves to maple-leaf-type leaves in the test cross $BC_1$ generation is 1:1. The above ratios indicate that the leaf shape character of maple-leaf-type conform to the genetic law of a pair of recessive genes, demonstrating that the leaf shape character of maple-leaf-type is controlled by a single recessive gene and belong to a discrete-character, and that the character is genetically stable and unaffected by environmental conditions. Photographs for leaf shape character segregation at the seedling stage are shown in FIG. 2.

TABLE 1

$F_2$ generation segregation test results

| | | | Materials | | | |
| --- | --- | --- | --- | --- | --- | --- |
| | | | South China type | | European type | |
| | Segregation ratio | North China type | Tangshan autumn cucumber | dry land cucumber | green cucumber | white cucumber |
| $F_2$ | direct-cross or reciprocal-cross $F_1$ | All being common leaves | All being common leaves | | All being common leaves | |
| | Theoretical ratio (common leaves:maple-leaf-type leaves) | 3:1 | 3:1 | 3:1 | 3:1 | 3:1 |
| | Actual number (theoretical number) (common leaves:maple-leaf-type leaves) | 37(36.75):12(12.25) | 41(36.75):8(12.25) | 41(37.5):9(12.5) | 38(37.5):12(12.5) | 37(37.5):13(12.5) |
| | $X_c^2$ | 0.01 | 1.97 | 1.31 | 0.03 | 0.3 |

TABLE 2

Test-cross test results about the character of maple-leaf-type leaf

| | | Materials | | | |
| --- | --- | --- | --- | --- | --- |
| | | South China type | | European type | |
| Segregation ratio | North China type | Tangshan autumn cucumber | Dry land cucumber | green cucumber | white cucumber |
| Theoretical ratio (common leaves:maple-leaf-type leaves) | 1:1 | 1:1 | 1:1 | 1:1 | 1:1 |

TABLE 2-continued

Test-cross test results about the character of maple-leaf-type leaf

| | Materials | | | | |
|---|---|---|---|---|---|
| | | South China type | | European type | |
| Segregation ratio | North China type | Tangshan autumn cucumber | Dry land cucumber | green cucumber | white cucumber |
| Actual number (theoretical number) (common leaves:maple-leaf-type leaves) | 22(24):26(24) | 22(25):28(25) | 24(25):26(25) | 24(23):22(23) | 25(25):25(25) |
| $X_c^2$ | 0.33 | 0.72 | 0.08 | 0.09 | 0 |

Example 2: Breeding Maple-Leaf-Type Cucumber Plant Variety by Hybridization

Maple-leaf-type cucumber plants were bred by using the cucumber plant CC81221 with maple-leaf-type leaves or the cucumber inbred lines derived therefrom and having maple-leaf-type leaves, $F_1$ hybrids or heterozygote as the donors of maple-leaf-type leaves. Therefore, any maple-leaf-type cucumber plant bred by the method of the present invention, and the plant CC81221 or the maple-leaf-type cucumber plant derived therefrom, all fall within the scope of the present invention.

(1) On May 25, 2012, an experiment was carried out in an experimental shed in Haidian district, Beijing. The experimental shed was closed and isolated with insect-proof nets. The maple-leaf-type cucumber material CC81221 was used as one of the parents, and three different types of common leaf inbred lines provided by Beijing Beinong Sanyi Cucumber Ecological Breeding Science and Technology Center, i.e. dense-thorn cucumber inbred line M1141 (palm-like pentagonal leaves), South China-type cucumber inbred line HA1151 (palm-like pentagonal leaves) and smooth and thornless fresh-eaten cucumber inbred line SG1131 (heart-like pentagonal leaves) were used as the other parent; the hybridization was carried out respectively by artificial pollination, and harvesting was carried out respectively to obtain $F_1$ generation seeds.

(2) On Sep. 15, 2012, $F_1$ generation seeds were planted in the experimental shed, inbred and harvested, respectively, to give $F_2$ generation seeds;

(3) On Jan. 15, 2013, $F_2$ generation seeds were planted in the experimental shed. According to the phenotypic segregation situation, maple-leaf-type plants with good agronomic characters or common leaf plants with good agronomic characters were selected for inbreeding. Harvesting was carried out respectively for each plants to give $F_3$ generation seeds.

(4) On May 25, 2013, the $F_3$ generation seeds were planted in the experimental shed, and among the $F_3$ generation population obtained from plants with maple-leaf-type leaves by inbreeding, plants were selected according to the target agronomic characters to perform inbreeding; the plants without the maple-leaf-type marker character were weed out, and with respect to the selected population of plants having maple-leaf-type leaves, the step (3) was repeated; and harvesting was carried out respectively for each plant to give $F_4$ generation seeds.

(5) On Sep. 25, 2013, the $F_4$ generation seeds were planted in the experimental shed, respectively, and the step (4) was repeated; and harvesting was carried out respectively for each plant to give $F_5$ generation seeds.

(6) On Jan. 15, 2014, the $F_5$ generation seeds were planted in the experimental shed, respectively, and the step (4) was repeated; and harvesting was carried out respectively for each plant to give $F_6$ generation seeds.

Figure 4:
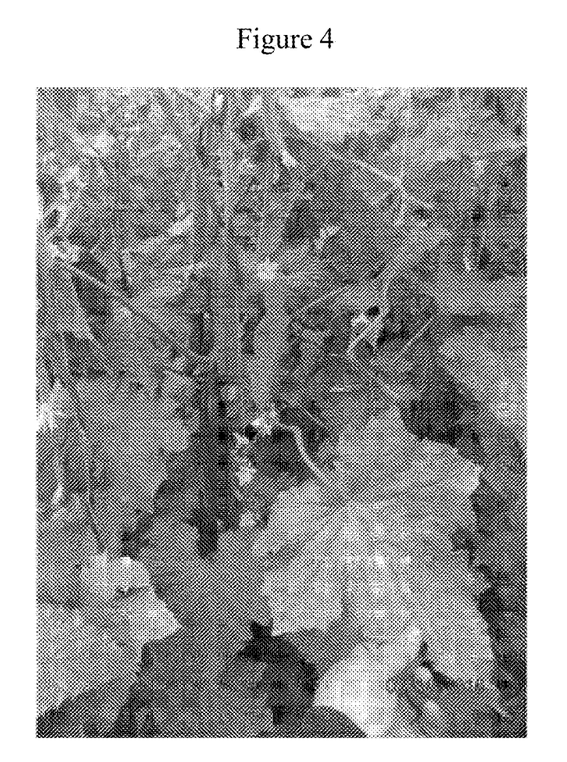
FIG. 4 shows a photograph of the CC81413 maple-leaf-type cucumber plants according to Example 2 in the field.
Figure 5:
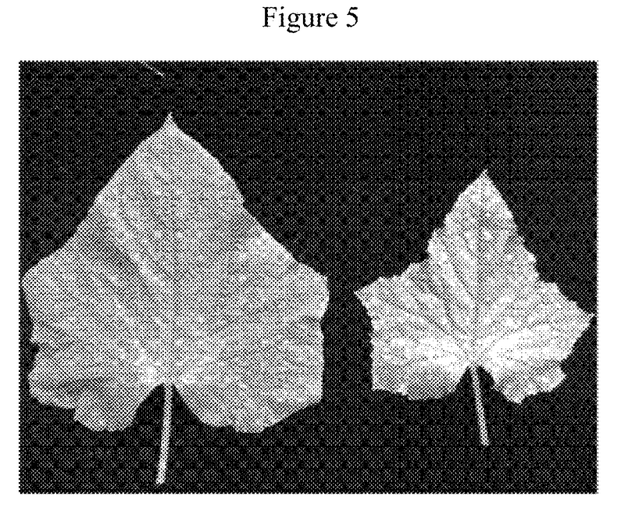
FIG. 5 shows the comparative photograph between the leaf of the CC81413 maple-leaf-type cucumber plant according to Example 2 and a common cucumber leaf, wherein the left one is the common cucumber leaf, and the right one is the leaf of the CC81413 maple-leaf-type cucumber plant.
Figure 6:
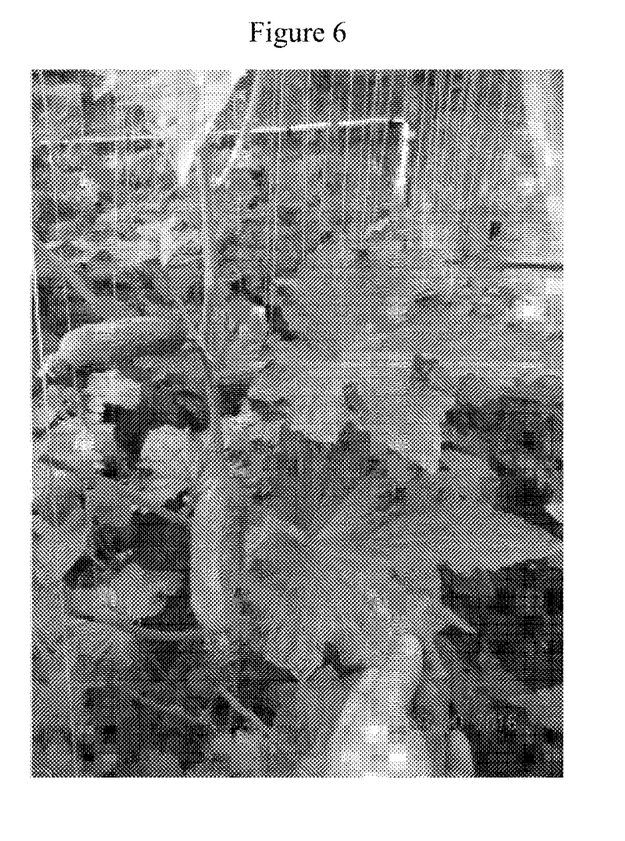
FIG. 6 shows a photograph of the CC81423 maple-leaf-type cucumber plants according to Example 2 in the field.
Figure 7:
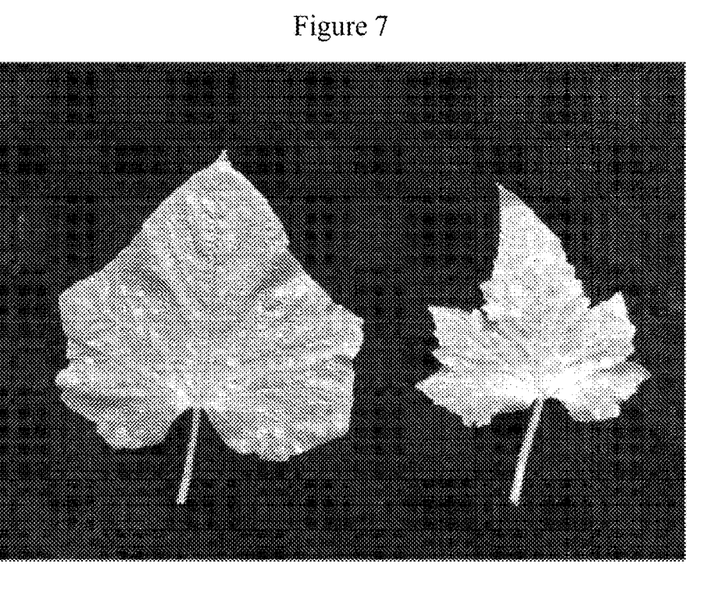
FIG. 7 shows the comparative photograph between the leaf of the CC81423 maple-leaf-type cucumber plant according to Example 2 and a common cucumber leaf, wherein the left one is the common cucumber leaf, and the right one is the leaf of the CC81423 maple-leaf-type cucumber plant.
Figure 8:
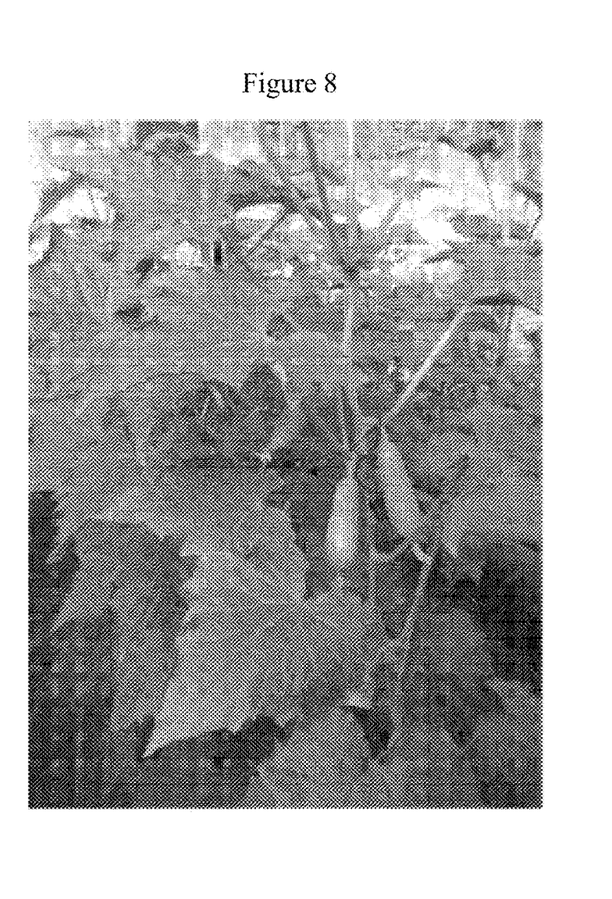
FIG. 8 shows a photograph of the CC81433 maple-leaf-type cucumber plants according to Example 2 in the field.
Figure 9:
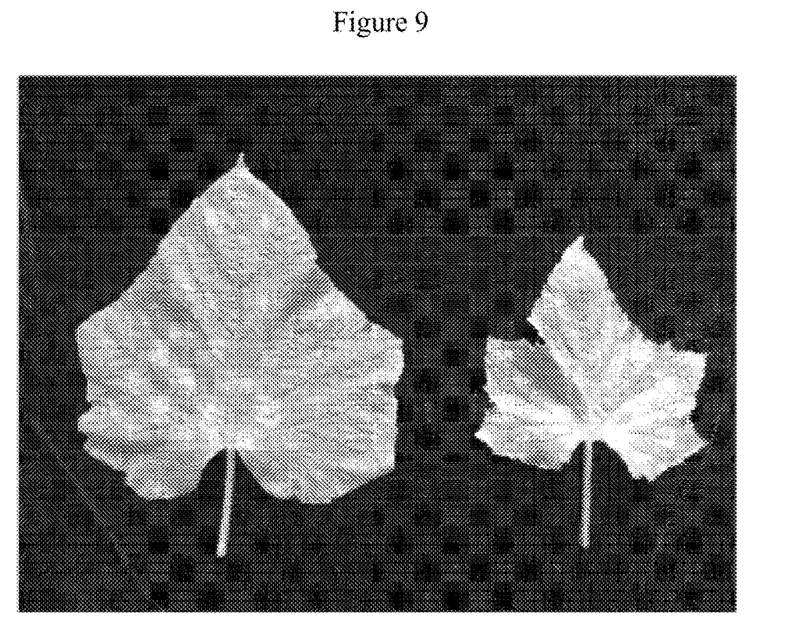
FIG. 9 shows the comparative photograph between the leaf of the CC81433 maple-leaf-type cucumber plant according to Example 2 and a common cucumber leaf, wherein the left one is the common cucumber leaf, and the right one is the leaf of the CC81433 maple-leaf-type cucumber plant.

(7) From May 2014 to September 2014, $F_6$ and $F_7$ generation seeds were planted, respectively, and step (4) was repeated to obtain homozygous and stable cucumber inbred lines with maple-leaf-type cleft leaves:

The dense-thorn maple-leaf-type inbred line CC81413 (photographs are shown in FIG. 4 and FIG. 5); the South China-type maple-leaf-type inbred line CC81423 (photographs are shown in FIG. 6 and FIG. 7); and the European smooth and thornless maple-leaf-type inbred line CC81433 (The photographs are shown in FIG. 8 and FIG. 9).

Example 3: Breeding of Maple-Leaf-Type Cucumber Varieties by Backcrossing Method The backcross method was used in the present invention for the primary purpose of altering or replacing the leaf shape of the original variety while substantially retaining all other desirable genetic, physiological and morphological composition of the original variety.

The character of maple-leaf-type leaves is controlled by a single recessive nuclear gene. In this case, the test directed to offspring must be introduced to the backcross transformation step, that is, the inbred offspring corresponding to each backcross generation was subjected to phenotypic test so as to determine which backcross plant carries the recessive gene encoding the maple-leaf-type leaves.

The backcrossing process could be simplified and speeded up by using molecular markers such as SSR, RFLP, SNP or AFLP markers.

(1) On May 25, 2012, in the test shed in Haidian district, Beijing, the maple-leaf-type cucumber plant CC81221 was used as the non-recurrent parent; the dense-thorn cucumber inbred line M1142 (palm-like pentagonal leaves) provided by Beijing Beinong Sanyi Cucumber Ecological Breeding Science and Technology Center was used as the recurrent parent to perform hybridization, so as to obtain $F_1$ generation seeds.

(2) On Sep. 15, 2012, the $F_1$ generation and the recurrent parent as described in step (1) were planted in the experimental shed, respectively, and backcross with the recurrent parent was carried out to obtain $BC_1F_1$ generation seeds.

(3) On Jan. 15, 2013, the $BC_1F_1$ generation and the recurrent parent were planted in an experimental shed, the individual plants with good agronomic characters were selected for self-crossing, the selected individual plants were used as the male parent to be back-crossed with the recurrent parent, and they were numbered correspondingly; and $BC_1F_2$ seeds and $BC_2F_1$ seeds were harvested for individual plants respectively.

(4) On May 25, 2013, the $BC_1F_2$ generation seeds and $BC_2F_1$ generation seeds were planted in an experimental shed, respectively, and the maple-leaf-type plants of the $BC_1F_2$ generation were selected and correspondingly numbered, and then an individual plant were selected for self-crossing; and the selected individual plant was used as the male parent to back-crossed with the recurrent parent, numbered correspondingly, and harvesting was carried out respectively for each plant to give $BC_2F_2$ generation seeds and $BC_3F_1$ generation seed, respectively.

Figure 10:
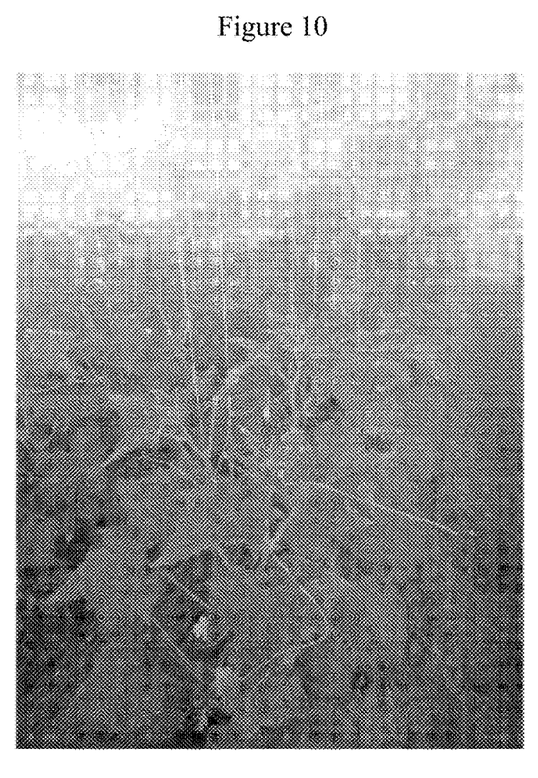
FIG. 10 shows a photograph of the MCC81411 maple-leaf-type cucumber plants according to Example 3 in the field.
Figure 11:
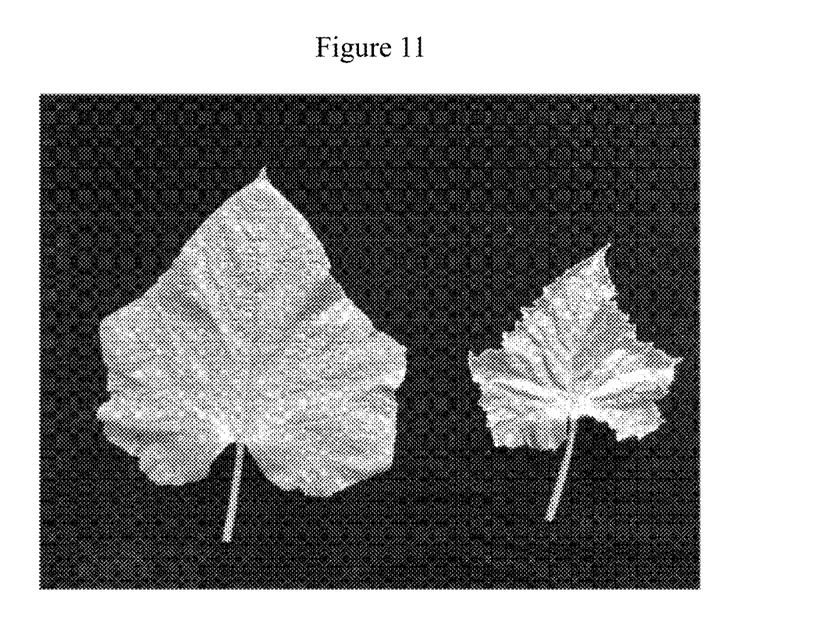
FIG. 11 shows the comparative photograph between the leaf of the MCC81411 maple-leaf-type cucumber plant according to Example 3 and a common cucumber leaf, wherein the left one is the common cucumber leaf, and the right one is the leaf of the MCC81411 maple-leaf-type cucumber plant.

(5) From Sep. 25, 2013 to January 2015, the step (4) was repeated for 2 to 8 generations in an experimental shed; when other characters of the $BC_nF_1$ (n represents the number of the generation) generation except for the leaf shape no longer segregated, self-crossing was carried out once to give the cucumber inbred line MCC81411 with maple-leaf-type leaves (FIG. 10 shows one photograph in the field, and FIG. 11 shows the comparative photograph between the leaf of the MCC81411 and a common cucumber leaf, wherein the left one is the common cucumber leaf, and the right one is the leaf of MCC81411).

Example 4: Test for Breeding Maple-Leaf-Type Cucumber Plant Hybrid with Maple-Leaf-Type Inbred Lines as Male and Female Parents Compared with the hybrids other than those of the present invention, hybrids bred in accordance with the methods of the present invention were characterized by hybridization using two cucumber parents having maple-leaf-type leaves. The purpose of this test was to achieve commercial production of hybrid seeds of cucumber plants with maple-leaf-type leaves. Specifically, the test included the following steps:

(1) From September 2012 to January 2015, in the experimental greenhouse in Haidian district, Beijing, the maple-leaf-type cucumber plant CC81221 was used as a non-recurrent parent, D2-4-1 (the female parent of Jintong (variety number: CNA 20100699.0)) and D2-4-31 (the male parent of Jintong (variety number: CNA20100699.0)) were used as maple-leaf-type receptors, respectively, and cucumber inbred line D2-4-1-CC3 (Maple-leaf-type Jingtong cucumber female parent) and D2-4-31-CC1 (Maple-leaf-type Jingtong cucumber male parent) having maple-leaf-type leaves were separately bred by the backcross transformation method as described in Example 3.

(2) Sowing and seedling were carried out on Feb. 5, 2015. On March 5, 4,000 plants per 667 square meters were planted with the ratio of male parent to female parent of 1:4. The hybridization was carried out by artificial pollination. On July 1st, the maple-leaf-type Jingtong cucumber hybrid was harvested.

(3) On Jul. 15, 2015, 500 seeds of each of Jintong cucumber and maple-leaf-type Jingtong cucumber were planted, and the seedlings were planted on August 1.

Figure 12:
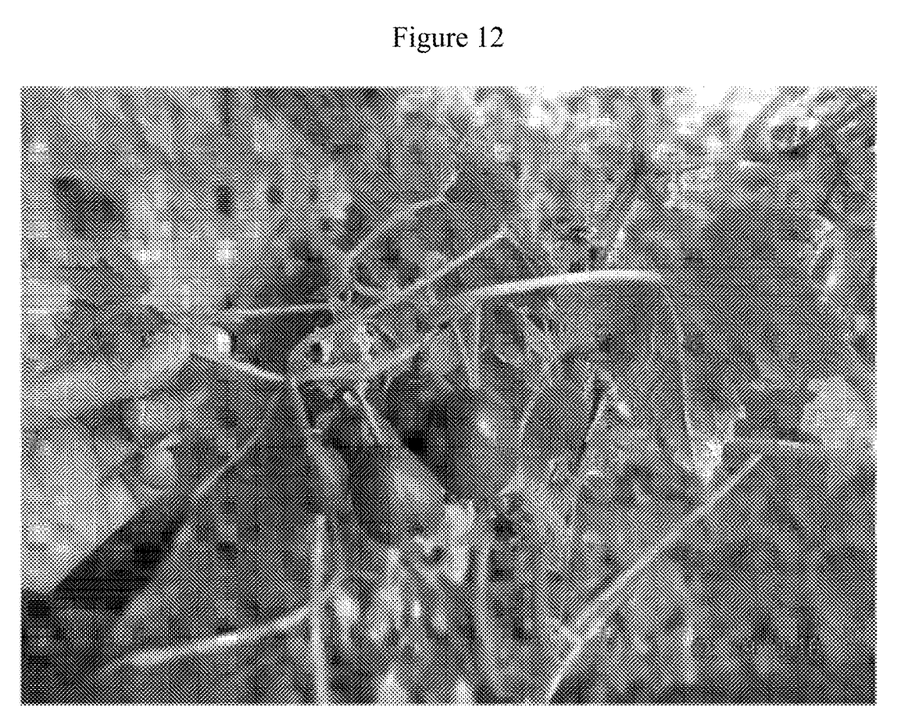
FIG. 12 shows a photograph of the maple-leaf-type Jingtong cucumber plants according to Example 4 in the field.
Figure 13:
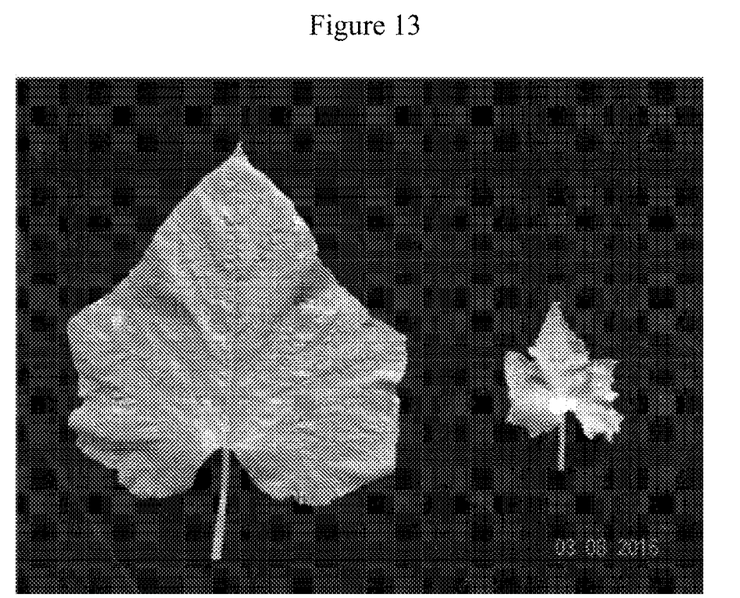
FIG. 13 shows the comparative photograph between the leaf of the maple-leaf-type Jingtong cucumber plant according to Example 4 and a common cucumber leaf, wherein the left one is the common cucumber leaf, and the right one is the leaf of the maple-leaf-type Jingtong cucumber plant.

(4) Phenotypic test for hybrid purity: comparing with the original Jintong cucumber in leaf shape, cucumber shape, cucumber color, female property, early maturity, disease resistance, yield and so on. The test was completed on October 15. The result shows that 100% of the plants are Jingtong cucumber having maple-leaf-type leaves, and the photographs are shown in FIG. 12 and FIG. 13.

Example 5: Test for Using SNP Molecular Marker to Assist Selection of the Gene for Maple-Leaf-Type Leaf (I) Test Materials:

Male parent: Mill (provided by Beijing Beinong Sanyi Cucumber Ecological Breeding Science and Technology Center): common leaves (dominant homozygous).

Female parent: CC81221 (accession number: CGMCC No. 11285), maple-leaf-type (recessive homozygous).

F1: common leaves (heterozygous).

(II) Test Methods:

1. Extraction of Leaf DNA

The DNA was extracted using the DNA Rapid Extraction Kit from Aidlab biotechnologies Co., Ltd, and the procedures were performed according to the instruction of the kit.

2. Cloning of Gene Fragment

The primer sequences used for SNP point mutation were as follows:

upstream primer: GTCCAGGTTCTCAATCGAGCT, as shown in SEQ ID No. 1;

downstream primer: GCCACGATATTGAGAGGTTCT, as shown in SEQ ID No. 2.

The reaction system for PCR amplification was given as follows:

| | |
|---|---|
| 10 µM upstream primer | 1 µl |
| 10 µM downstream primer | 1 µl |
| DNA | 2 µl |
| Premixture (Beijing Liuhetong Trading Co., Ltd., trade name: Premix Taq, product RR901A) | 12.5 µl |
| Sterilized water | the remainder |

The total reaction system was 25 µl.

The reaction conditions for the PCR amplification were given as follows:

Pre-denaturation at 94° C. for 2 min; 30 cycles of denaturation at 94° C. for 30 sec, annealing at 56° C. for 45 sec, and extension at 72° C. for 2.0 min; extension at 72° C. for 15 min, ending at 4° C.

3. Sequencing of PCR Product

Figure 14:
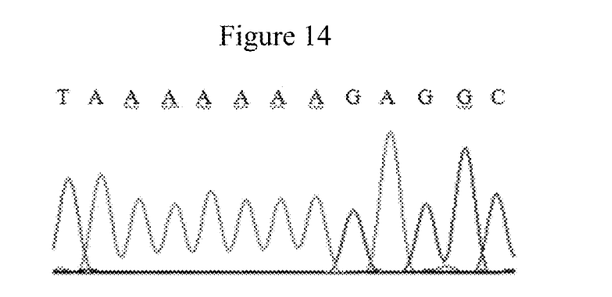
FIG. 14 shows a peak diagram of sequencing result of the male paternal in Example 5 using SNP marker.
Figure 15:
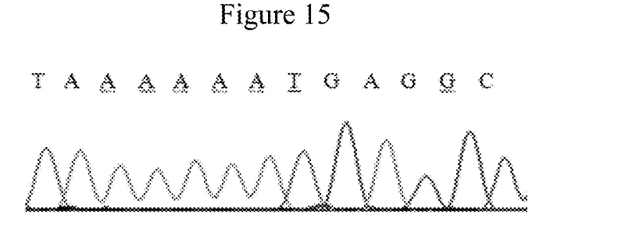
FIG. 15 shows a peak diagram of sequencing result of the female paternal in Example 5 using SNP marker.
Figure 16:
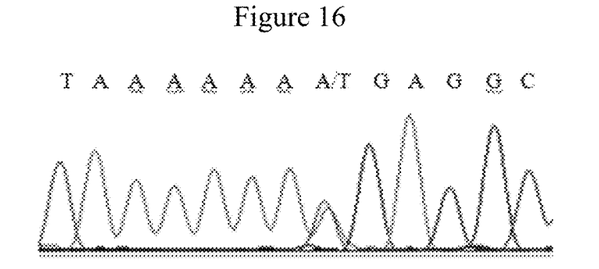
FIG. 16 shows a peak diagram of sequencing result of the F1 generation in Example 5 using SNP marker.

The amplification product was sent for sequencing, and the results were shown in FIG. 14 (male parent; SEQ ID NO: 3-TAAAAAAAGAGGC, wherein the A at the 8$^{th}$ position corresponds with position 859), FIG. 15 (female parent; SEQ ID NO: 4-TAAAAAATGAGGC, wherein the T at the 8$^{th}$ position corresponds with position 859), and FIG. 16 (F1;

SEQ ID NO: 5-, wherein the A/T at the 8$^{th}$ position corresponds with position 859), which indicate that the SNP molecular marker can mark the cucumber plants having the single recessive nuclear gene for maple-leaf-type leaf.

Although the present invention has been described in detail by general description and specific embodiments, it will be apparent to a person skilled in the art that some modifications and improvements can be made based on the present invention. Therefore, such modifications or improvements made without departing from the spirit of the invention are intended to be within the scope of the invention.

INDUSTRIAL APPLICABILITY

The present invention discloses a maple-leaf-type cucumber plant, which is a mutant cucumber plant CC81221 having maple-leaf-type cleft leaves and found in the process of hybridization and breeding, or a cucumber plant derived therefrom and having a single recessive nuclear gene for maple-leaf-type leaf. The present invention provides a cucumber leaf mutant plant having maple-leaf-type cleft leaves and found in the process of hybridization and breeding. The present invention provides the derivatives of those plants and plant parts thereof, and also provides the application method of these plants. The significance of the present invention lies in that: the present invention discloses that the genetic character of having such maple-leaf-type leaves is a discrete character controlled by a single recessive nuclear gene, and discloses the morphological characteristic and molecular marker of the character. With the present invention, in the process of breeding a new variety of cucumber, the cucumber plant character of maple-leaf-type leaves can be more simply introduced to different kinds of varieties by conventional breeding methods, compared with quantitative characters that are controlled by plural genes, such as leaf area, thereby solving various breeding contradictions of populations, such as the contradiction between planting density and photosynthetic efficiency, the contradiction between vegetative growth and reproductive growth, which are prevalent but difficult to balance in cucumber production. The purpose of improving marketability, disease resistance, yield and the like can also be achieved by enhancing ventilating and light transmitting effect. The present invention also provides a new character usable for breeding beautiful and high-ornamental value cucumber varieties.

What is claimed is:

1. A homozygous maple-leaf-type cucumber plant, characterized in that, it is:
    1) a cucumber mutant plant having a single recessive nuclear gene for maple-leaf-type leaf, which is a *Cucumis* plant CC81221 with the accession number CGMCC No. 11285, or
    2) a cucumber plant derived from CC81221 and having a single recessive nuclear gene for maple-leaf-type leaf;
    wherein, the single recessive nuclear gene for maple-leaf-type leaf is a single gene located at the base position of 16383700 to 16385719 on the second chromosome of the cucumber genome, and the base A at position 859 is mutated to T compared with the gene of cucumbers with a common leaf shape, wherein position 859 is the 8$^{th}$ position in SEQ ID NO: 5.

2. A part of the maple-leaf-type cucumber plant according to claim 1, wherein the part is plant cells, seeds, anthers, pollen, ovules, leaves, germs, roots, root tips, flowers, fruits, stems, shoots, scion, protoplasts or calluses.

3. A method for breeding a homozygous maple-leaf-type cucumber plant variety, characterized in that, the maple-leaf-type cucumber plant variety is bred using CC81221 or a cucumber plant derived from CC81221 and having a single recessive nuclear gene for maple-leaf-type leaf as a genetic source of the maple-leaf type,
    wherein the single recessive nuclear gene for maple-leaf-type leaf is a single gene located at the base position of 16383700 to 16385719 on the second chromosome of the cucumber genome, and the base A at position 859 is mutated to T compared with the gene of cucumbers with a common leaf shape, wherein position 859 is the 8$^{th}$ position in SEQ ID NO: 5.

* * * * *